(12) United States Patent
Vinod et al.

(10) Patent No.: US 6,933,405 B2
(45) Date of Patent: Aug. 23, 2005

(54) USER- AND ECO-FRIENDLY HYPERVALENT IODINE REAGENT AND METHOD OF SYNTHESIS

(75) Inventors: Thottumkara K. Vinod, Macomb, IL (US); Arun P. Thottumkara, Macomb, IL (US)

(73) Assignee: Board of Trustees of Western Illinois University, Macomb, IL (US)

( * ) Notice: Subject to any disclaimer, the term of this patent is extended or adjusted under 35 U.S.C. 154(b) by 190 days.

(21) Appl. No.: 10/632,016

(22) Filed: Jul. 31, 2003

(65) Prior Publication Data

US 2004/0030187 A1 Feb. 12, 2004

Related U.S. Application Data

(60) Provisional application No. 60/400,320, filed on Jul. 31, 2002.

(51) Int. Cl.[7] .......................... C07C 45/29; C07C 45/30; C07C 65/00
(52) U.S. Cl. ....................... 562/405; 568/319; 568/323; 568/435; 568/437; 568/484
(58) Field of Search .......................... 562/405; 568/319, 568/323, 435, 437, 484

(56) References Cited

PUBLICATIONS

Takizawa, Hirofumi Tohma, et al.; Facile and Clean Oxidation of Alcohols in Water Using Hypervalent Iodine(III) Reagents; Angew. Chem. Int. Ed.; 2000; pp. 1306–1308; vol. 7; Issue 39; Wiley–VCH Verlag GmbH; Weinheim Germany.

Togo, Hideo, et al.; Preparation and Reactivities of Novel (Diacetoxyiodo)arenes Bearing Heteroaromatics; J. Org. Chem; 2000; pp. 8391–8394; vol. 65; American Chemical Society; USA.

Frish, Limor, et al.; A Pulsed Gradient Spin Echo NMR Study of Guest Encapsulation by Hydrogen–Bonded Tetraurea Calix[4]arene Dimers; J. Chem. Soc., Perkin Trans. 2; 1999; pp. 669–671.

De Mico, Antonella, et al.: A Versatile and Highly Selective Hypervalent Iodine (III)/2,2,6, 6–Tetramethyl–1–piperidinyloxyl–Mediated Oxidation of Alcohols to Carbonyl Compounds; J. Org. Chem; 1997; pp. 6974–6977; vol./Issue 62; American Chemical Society; USA.

Frigerio, Marco, et al.; Oxidation of Alcohols With o–Iodoxybenzoic Acid (IBX) in DMSO: A New Insight into an Old Hypervalent Iodine Reagent; J. Org. Chem.; 1995; vol./Issue 60; pp. 7272–7276; American Chemical Society: USA.

Dess, Daniel B., et al.; A Useful 12–I–5 Triacetoxyperiodinane (the Dess–Martin Periodinane) for the Selective Oxidation of Primary or Secondary Alcohols and a Variety of Related 12–I–5 Species[ta]; J. Am. Chem. Soc.; 1991; vol./ Issue 113; pp. 7277–7287; American Chemical Society; USA.

Dess, D.B., et al.; Readily Accessible 12–I–5[′] Oxidant for the Conversion of Primary and Secondary Alcohols to Aldehydes and Ketones; J. Org. Chem.; 1983; vol./Issue 48; pp. 4155–4156; American Chemical Society; USA.

Meyer, Stephanie D., et al.; Accelleration of the Dess–Martin Oxidation by Water; J. Org. Chem.; 1994; vol./Issue 59; pp. 7549–7552; American Chemical Society; USA.

Frigerio, Marco, et al.; A User–Friendly Entry to 2–Iodoxybenzoic Acid (IBX); J. Org. Chem.; 1999; vol./Issue 64; pp. 4537–4538; American Chemical Society; USA.

Nicolaou, K.C., et al.; New Synthetic Technology for the Construction of N–Containing Quinones and Derivatives Thereof; Total Synthesis of Epoxyquinomycin B; Angew. Chem. Int. Ed.; 2001; pp. 207–210;vol. 40; Issue 1; Wiley–VCH Verlag GmbH; Weinheim Germany.

Nicolaou, K.C., et al.; New Synthetic Technology for the Rapid Construction of Novel Heterocycles—Part 1: The Reactoin of Dess–Martin Periodinane with Anilides and Related Compounds; Angew. Chem. Int. Ed.; 2000; pp. 622–625; vol. 39; Issue 3; Wiley–VCH Verlag GmbH; Weinheim Germany.

Nicolaou, K.C., et al.; New Synthetic Technology for the Rapid Construction of Novel Heterocycles—Part 2: The Reaction of IBX with Anilides and Related Compounds; Angew. Chem. Int. Ed.; 2000; vol. 39; Issue 3; p. 625–628, Wiley–VCH Verlag GmbH; Weinheim Germany.

Nicolaou, K.C., et al; Novel IBX–Mediated Processes for the Synthesis of Amino Sugars and Libraries Thereof; Angew. Chem. Int. Ed.; 2000; pp. 2525–2529; vol. 39; Issue 14; Wiley–VCH Verlag GmbH; Weinheim Germany.

(Continued)

*Primary Examiner*—Bernard Dentz
(74) *Attorney, Agent, or Firm*—Blackwell Sanders Peper Martin LLP

(57) ABSTRACT

The present invention is a user- and eco-friendly hypervalent iodine reagent (mIBX) capable of selectively oxidizing allylic and benzylic alcohols in water and other eco-friendly solvents and having generally the following structure:

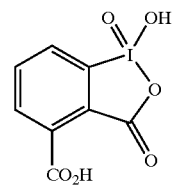

Allylic and benzylic alcohols are cleanly oxidized to the corresponding carbonyl compounds in water or water-THF mixtures, or other mixtures, using a water-soluble o-iodoxybenzoic acid derivative of the present invention.

7 Claims, 3 Drawing Sheets

PUBLICATIONS

Nicolaou, K.C., et al.; A New Method for the One–Step Synthesis of αβ–Unsaturated Carbonyl Systems from Saturated Alcohols and Carbonyl Compounds; J. Am. Chem. Soc.; 2000; pp. 7596–7597; vol./Issue 122; American Chemical Society; USA.

Nicolaou, K.C. et al.; Selective Oxidation of Carbon Adjacent to Aromatic Systems with IBX; J. Am. Chem. Soc.; 2001; pp. 3183–3185; vol./Issue 123; American Society; USA.

Ritter, Stephen K.; Green Chemistry; Chemical & Engineering News; Jul. 16, 2001; pp. 27–34; USA.

Li/ Chao–Jun; Organic Reactions in Aqueous Media—With Focus on Carbon–Carbon Bond Formation; Chem. Rev.; 1993; pp. 2023–2035; vol./Issue 93; American Chemical Society; USA.

Reagents and conditions: (a) (i) SOCl₂, heat, (ii) CH₃OH, heat, 100%; (b) H₂ (55 psi), Pd-C, CH₃OH, 100%; (c) (i) NaNO₂, HCl, 0-5°C, (ii) KI, 91%; (d) (i) NaOH, THF-H₂O (3:1v/v), (ii) aq. HCl, 93%; (e) KBrO₃, 0.73 M H₂SO₄, 55°C, 3 h, 70%.

| Entry | Substrate | Product | Conditions[a] | % Yield |
|---|---|---|---|---|
| 1 | ~~~OH cis-trans mixture | ~~~CHO cis-trans mixture | 1:2, H₂O, RT, 18 h | 86[b] |
| 2 | ~~~~OH | ~~~~CHO | 1:2, H₂O, RT, 18 h | 90[b] |
| 3 | Ph-CH=CH-CH₂OH | Ph-CH=CH-CHO | 1:2, H₂O, RT, 18 h | 80 |
| 4 | PhCH₂OH | PhCHO | 1:1.5, H₂O, 60°C, 3 h | 95 |
| 5 | 4-O₂N-C₆H₄-CH₂OH | 4-O₂N-C₆H₄-CHO | 1:1.5, H₂O:THF (5:2 v/v)[c], 60°C, 3 h | 79 |
| 6 | 4-Br-C₆H₄-CH₂OH | 4-Br-C₆H₄-CHO | 1:1.5, H₂O:THF (5:2 v/v)[c], 60°C, 3 h | 69 |
| 7 | 4-H₃CO-C₆H₄-CH₂OH | 4-H₃CO-C₆H₄-CHO | 1:1.5, H₂O, 60°C, 3 h | 95 |
| 8 | 1,2-(HOCH₂)₂C₆H₄ | 1,2-(OHC)₂C₆H₄ | 1:2.5, H₂O, 60°C, 3 h | 80 |
| 9 | 3-O₂N-C₆H₄-CH(OH)CH₃ | 3-O₂N-C₆H₄-C(O)CH₃ | 1:1.5, H₂O:THF (4:3 v/v)[c], 60°C, 3 h | 96 |
| 10 | PhCH(OH)CH(OH)Ph | PhC(O)C(O)Ph | 1:2.5, H₂O:THF (3:3 v/v)[c], 60°C, 3 h | 81 |
| 11 | PhCH(OH)CH₂OH | PhC(O)CH₂OH | 1:1, H₂O, 60°C, 3 h | 60[d] |
| 12 | HOCH₂-C₆H₄-O-CH₂CH(OH)CH₂-C₆H₄-OCH₃ | OHC-C₆H₄-O-CH₂CH(OH)CH₂-C₆H₄-OCH₃ | 1:2 H₂O, 60°C, 3 h | 84 |

[a] Reaction conditions are noted in the following order: Substrate to mIBX ratio, solvent(s), temperature, time

[b] The yield reported for entries 1 and 2 are calculated using gas chromatography. The other yields reported in Table 1 are isolated yields.

[c] Formation of γ-butyrolactone (~10%), via oxidation of THF, was observed from reactions carried out in the mixed solvent system

[d] Nearly 25% of phenylglyoxalic acid was also isolated from this reaction.

FIG. 2

Mechanism of oxidation of benzylic/allylic alcohols in water using mIBX.

USER- AND ECO-FRIENDLY HYPERVALENT IODINE REAGENT AND METHOD OF SYNTHESIS

CROSS-REFERENCE TO RELATED APPLICATIONS

This application claims benefit of U.S. Provisional Application Ser. No. 60/400,320, filed Jul. 31, 2002.

BACKGROUND OF INVENTION

The present invention relates generally to hypervalent iodine reagents and, more specifically, to a user- and eco-friendly hypervalent iodine reagent, mIBX, and the synthesis thereof.

Hypervalent iodine reagents, due to their low toxicity and ready availability, have attracted considerable attention recently as mild and selective oxidizing agents. Of the various hypervalent iodine reagents known, Dess-Martin periodinane (DMP), and o-iodoxybenzoic acid (IBX) are the most commonly used. Despite the nontoxic nature of these compounds and their ease of preparation, these reagents have certain drawbacks. Both reagents are potentially explosive, and thus cannot be stocked in large quantities. In addition to this drawback, oxidation of alcohols using DMP is carried out in environmentally unsafe chlorinated solvents and reactions employing IBX are often limited in dimethyl sulfoxide (DMSO) due to the reagent's insolubility in other common organic solvents. While oxidation reactions using both DMP and IBX tolerate the presence of moisture in the reaction medium, the presence of large amounts of water, when used as a solvent or co-solvent, is detrimental to the outcome of the oxidation reactions using these reagents. This is due to the fact that the mechanisms of oxidation with both the oxidizing agents involve reactive intermediates formed in an equilibrium step that is disfavored with increasing concentrations of water.

A series of papers from Nicolau Laboratories have recently identified several new oxidative transformations, including a selective oxidation of benzylic carbons using IBX. These reactions were carried out in either DMSO or fluorobenzene/DMSO mixtures. Single electron transfer (SET) reaction pathways have been proposed for these synthetic technologies. A significant aspect of the new oxidative transformations is that the presence of water does not affect the outcome of these reactions. Due to the ever-growing demand for eco-conscious chemical processes, there is a need for a water-soluble derivative of IBX that can behave as a green-oxidant capable of oxidizing alcohols in water. The present invention provides such a derivative, as well as a method of synthesizing the same via a SET mechanism similar to the synthesis of a water-soluble derivative of IBX, referred to herein as modified IBX (mIBX), and oxidation of the allylic and benzylic alcohols using mIBX in water and other eco-friendly solvents.

REFERENCES

Varvoglis, A. *Hypervalent Iodine in Oranigc Synthesis*, Academic Press: San Diego (1997).

Tohma, H.; Takizawa, S.; Maegawa, T.; Kita, Y., *Angew. Chem., Intl. Ed.*2000, 39,1306–1308.

Togo, H; Nabana, T.; Yamaguchi, K.,*J. Org. Chem.,* 2000, 65, 8391–8394.

Ley, S. V.; Thomas, A. W.; Finch, H., *J. Chem. Soc., Perkin Trans. I,* 1, 1999, 669–671.

De Mico, A.; Margarita, R.; Parlanti, L.; Vescovi, A; Piancatelli, G., *J. Org. Chem.,* 1997, 62, 6974–6977.

Corey, E. J.; Palani, A., *Tetrahedron Lett.,* 1995, 36, 7945–7948.

Frigerio, M.; Santagostino, M.; Sputore, S.; Palmisano, G., *J. Org. Chem.,* 1995, 60, 7272–7276.

Dess, D. B.; Martin, J. C., *J. Am. Chem. Soc.,* 1991, 113, 7277–7287.

Dess, D. B.; Martin, J. C., *J. org. Chem.,* 1983, 48, 4155–4156.

Meyer, S. D.; Schriber, S. L., *J. Org. Chem.,* 1994, 59, 7549–7552.

Hartman, C.; Meyer, V., *Chem. Ber.,* 1893, 26, 1727.

Friegerio, M.; Santagostino, M.; Supatore, S., *J. Org. Chem.,* 1999, 64, 4537–4538.

Nicolau, K. C.; Sugita, K.; Baran, P. S.; Zhong, Y.-L., *Angew. Chem., Int. Ed.,* 2001, 40, 207–210.

Nicolau, K. C.; Zhong, Y.-L.; Baran, P. S.,*Angew. Chem., Int. Ed.,* 2000, 39, 622–625.

Nicolau, K. C.; Zhong, Y.-L.; Baran, P. S.,*Angew Chem., Int. Ed.,* 2000, 39, 625–628.

Nicolau, K. C.; Baran, P. S.; Zhong, Y.-L.; Vega, J., *Angew. Chem., Int. Ed.,* 2000, 39, 2525–2529.

Nicolau, K. C.; Zhong, Y.-L.; Baran, P. S., *J. Am. Chem. Soc.,* 2000, 122, 7596–7597.

Nicolau, K. C.; Baran, P. S.; Zhong, Y.-L., *J. Am. Chem. Soc.,* 2001, 123, 3183–3185.

*Green Chemistry*, Chemical and Engineering News, 2001, Jul. 16, 27–34.

*Organic Synthesis in Water*; Grieco, P. A., Ed, Blackie Academic: London, 1998.

Li, C.-J., *Chem. Rev.,* 1993, 2023–2035

Corey, E. J.; Palani, A., *Tetrahedron Lett.,* 1995, 36, 3485–3488.

SUMMARY OF INVENTION

The present invention relates to a user- and eco-friendly hypervalent iodine reagent capable of selectively oxidizing allylic and benzylic alcohols in water and other eco-friendly solvents, and the synthesis thereof. The oxidation protocol using this chemoselective reagent is operationally simple, providing good to excellent yields of carbonyl compounds.

The modified iodoxybenzoic acid (mIBX) of the present invention offers several advantages over the current use of o-iodoxybenzoic acid. For instance, oxidation reactions using mIBX can be performed in aqueous media as opposed to organic solvents, thereby making mIBX attractive for large-scale industrial oxidation reactions by allylic and benzylic alcohols. The present invention therefore overcomes the limitations of waste management of the organic solvents used when iodoxybenzoic acid is used for these oxidation reactions. Surprisingly, mIBX exhibits unexpected selectivity for the oxidation of allylic and benzylic alcohols. Iodoxybenzoic acid, on the other hand, oxidizes all primary and secondary alcohols in organic solvents only, and does not exhibit the unique selectivity exhibited by mIBX for allylic and benzylic alcohols. Furthermore, the separation of the reduced form of mIBX from the aqueous reaction medium is facilitated by precipitation of the reduced form, thereby making the isolation of the desired oxidation product as well as recovery of the reduced form of mIBX easy. More importantly, the easily recovered reduced form of mIBX can be recycled to the original form oxidizing agent, making the overall process very cost effective in multiple steps.

BRIEF DESCRIPTION OF DRAWINGS

FIG. 2 illustrates the results of oxidation of various allylic and benzylic alcohols using mIBX.

DETAILED DESCRIPTION

Figure 1:
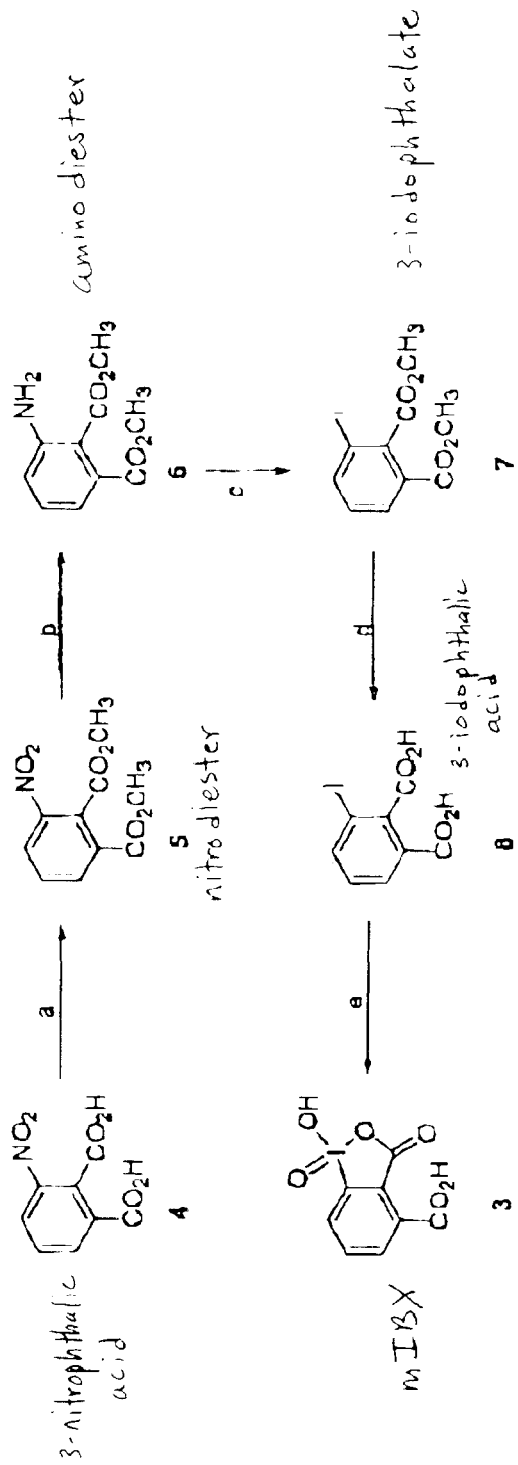
FIG. 1 illustrates a chemical pathway detailing the synthesis of mIBX from 3-nitrophthalic acid.

The synthesis of mIBX is readily accomplished from commercially available 3-nitrophthalic acid as follows: esterification of 3-nitrophthalic acid via the corresponding acid chloride to give nitrodiester (100%), which upon catalytic hydrogenation provides the aminodiester (100%). Diazotization is then performed, followed by iodination of the aminodiester to provide dimethly 3-iodophthalate in about 91% yield. This is followed by saponification, then acidification of dimethyl 3-iodophthalate to give 3-iodophthalic acid in about 93% yield. 3-iodophthalic acid is then oxidized to form the water-soluble mIBX. This process is carried out using $KBrO_3$ in $0.73H_2SO_4$ at 55–60° C. as follows: $KBrO_3$ (5 g, 30 mmol) is added in portions to a suspension of 3-iodophthalic acid (5 g, 17.1 mmol) in 70 mL of 0.73 M $H_2SO_4$ over a period of 20 minutes; The mixture is then maintained at 55–60° C. for 12 hours and the resulting clear orange solution is evaporated to yield an off-white solid, which is triturated with 30 mL of water at 0° C. for 2 hours and filtered to obtain a white solid. This is further triturated with hexane (100 mL) for 6 hours and filtered to give mIBX (3.9 g, 71%) as a white solid with a melting point of 258–260° C. The approximately 70% yield for the conversion of 3-iodophthalic acid to mIBX is the isolated yield of mIBX, with the actual conversion near quantitative as evident from monitoring the oxidation of 3-iodophthalic acid to mIBX by $^1$H NMR spectroscopy. Water-soluble mIBX is isolated as an analytically pure white solid. The synthesis of mIBX from 3-nitrophthalic acid is illustrated in FIG. 1.

The physical properties of mIBX are as follows: mp 258–260° C.; IR (KBr), 3503 3469, 3050, 1708, 1631, 1588, 1369, 730, 700 $cm^{-1}$; $^1$H NMR ($D_2O$), 300 MHz): δ 8.35 (dd, J=7.9, 1.0 Hz, 1H), 8.09 (t, J=7.9 Hz, 1H), 7.94 (dd, J=7.9, 1.0 Hz, 1H); $^{13}$C NMR ($D_2O$, 75 MHz): δ 125.5, 127.5, 132.5, 134.7, 137.0, 147.1 (ring carbons), 168.9, 172.9 (carbonyl carbons).

The mIBX compound of the present invention is useful as a green-oxidant, as indicated by monitoring the oxidation of benzyl alcohol, 2-hexanol, 2-phenylethanol, and cyclohexanol using $^1$H NRM and using $D_2O$ as the solvent. The selective oxidation of allylic and benzylic alcohols from this short list of substrates reflects an unexpected property of the present invention. The limitations of the new reagent in terms of its selectivity and compatibility with other functional groups was established by studying the oxidation of a series of allylic and benzylic alcohols. The results are summarized in FIG. 2. Tetrahydrofuran (THF) was used as co-solvent when necessary without impeding the effectiveness of the reagent.

As evident from FIG. 2, mIBX efficiently oxidizes a variety of allylic and benzylic alcohols and tolerates the presence of a series of functional groups during the oxidation. Over-oxidation products are not observed, even when electron rich substituents are present on the ring (FIG. 2, entry 7). Monitoring the progress of the oxidation of 1,2-benzenedimethanol (FIG. 2, entry 8) indicated that the presence of the electron withdrawing formyl group (formed in the course of the oxidation) did not adversely affect the rate or the yield of the final dialdehyde product. Oxidation of the same substrate using IBX in DMSO gives the corresponding lactol as the product, clearly delineating the difference in the mechanism of oxidation using the two structurally analogous reagents in two different solvents. Presence of electron withdrawing groups also does not affect the rate or the yield of the final product (FIG. 2, entries 5 and 9). Oxidation of vicinal diols occurs without accompanied oxidative cleavage (FIG. 2, entries 10 and 11). Oxidation of 1-phenyl-1,2-ethanediol (FIG. 2, entry 11) gives 55–60% isolated yield of 2-hydroxyacetophenone indicating the unexpected selectivity of mIBX towards benzylic OH groups. This particular oxidation carried out with a 1:1 substrate to mIBX ratio also gives 20–25% yield of benzoylformic acid, an apparent over-oxidation product. The selectivity of mIBX towards benzylic OH groups is also noted in the oxidation of non-vicinal diol (FIG. 2, entry 12) to the corresponding benzaldehyde.

Figure 3:
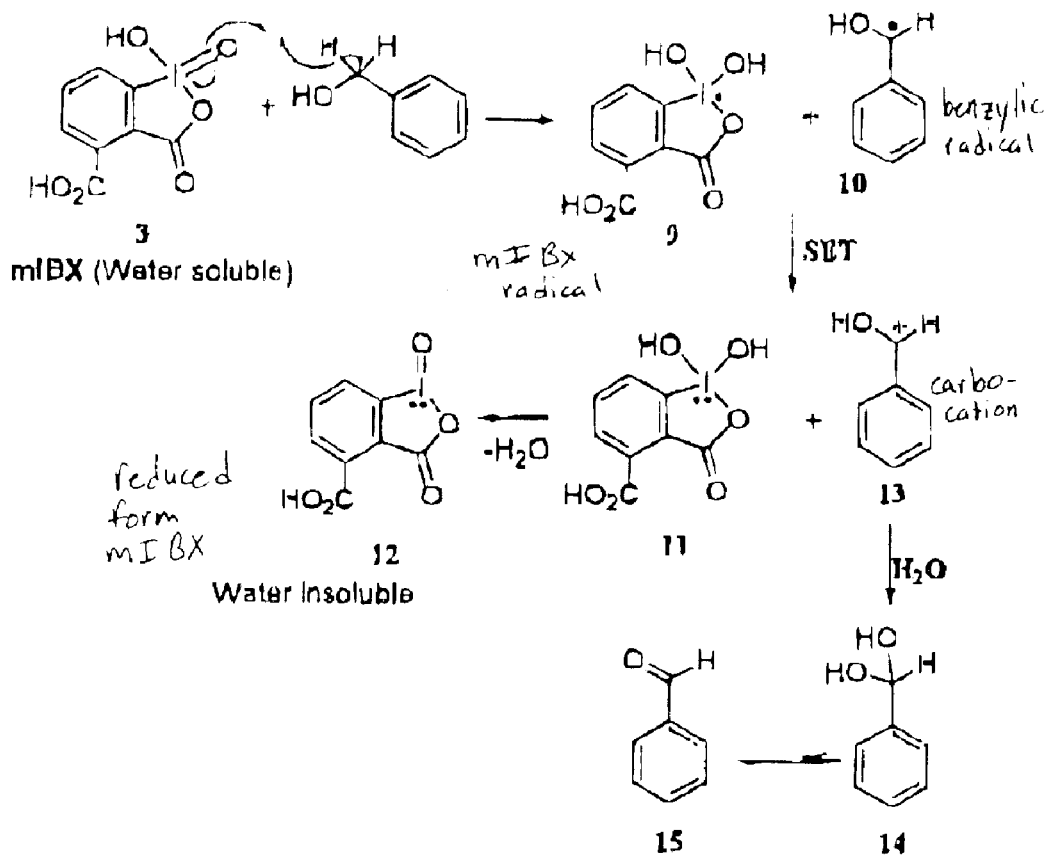
FIG. 3. Illustrates a mechanism of oxidation of benzylic/allylic alcohols in water using mIBX.

A proposed mechanism for the oxidation of allylic and benzylic alcohols is illustrated in FIG. 3. The salient features of this mechanism include the α-H abstraction from benzyl alcohol by mIBX to give mIBX radical and a benzylic radical. A subsequent SET from the benzylic radical to mIBX radical generates the carbocation, which then gives benzaldehyde. An important aspect of this oxidation protocol is the nearly complete insolubility of the reduced form of mIBX in water, which allows for easy removal of the spent reagent by filtration. The work-up of oxidation reactions carried out in water using mIBX thus involves only filtration and a subsequent removal of the solvent. An easy re-oxidation of the reduced form of mIBX to mIBX, using $KBrO_3$ makes the procedure cost-effective as well.

It is understood that the description and examples above are exemplary in nature and are not intended to be limiting. Changes and modifications to the present invention may be apparent to one skilled in the art upon reading this disclosure, and such changes and modifications may be made without departing from the spirit and scope of the present invention.

What is claimed is:

1. A modified iodoxybenzoic acid compound having generally the following structure:

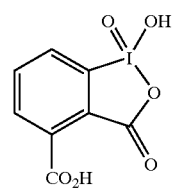

2. A method of synthesizing a modified iodoxybenzoic acid compound from 3-nitrophthalic acid comprising:

(a) esterification of 3-nitrophthalic acid using a corresponding acid chloride, to produce a nitrodiester;

(b) catalytic hydrogenation of said nitrodiester, to produce an aminodiester;

(c) diazotization of said amonidiester by iodination of said aminodiester, to produce dimethly 3-iodophthalate;

(d) saponification of said dimethly 3-iodophthalate;

(e) acidification of said dimethly 3-iodophthalate, to produce 3-iodophthalic acid; and (f) oxidation of said 3-iodophthalic acid to produce a modified iodoxybenzoic acid compound having generally the following structure:

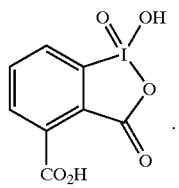

3. A method of oxidizing a substrate comprising reacting said substrate with a modified iodoxybenzoic acid compound having generally the following structure:

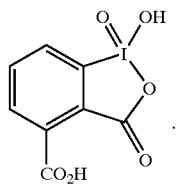

4. The method of claim 3 wherein said substrate is an allylic alcohol.

5. The method of claim 3 wherein said substrate is a benzylic alcohol.

6. The method of claim 3 wherein the oxidation reaction between said substrate and said modified iodoxybenzoic acid compound takes place in an aqueous solution.

7. The method of claim 3 wherein said substrate is selected from the group consisting of 2-Buten-1-ol, trans-2-Hexen-1-ol, trans-3-Phenyl-2-propen-1-ol, Hydroxymethylbenzene, 4-Nitrobenzenemethanol, 4-Bromobenzenemethanol, 4-Methoxybenzenemethanol, 1,2-Benzenedimethanol, 1-(3-Nitrophenyl)ethanol α-Methyl-3-nitrobenzenemethanol, 1,2-Diphenyl-1,2-ethanediol, 1-Phenyl-1,2-ethanediol and 4-(3-Hydroxypropoxy)benzenemethanol.

* * * * *

UNITED STATES PATENT AND TRADEMARK OFFICE
CERTIFICATE OF CORRECTION

PATENT NO. : 6,933,405 B2
DATED : August 23, 2005
INVENTOR(S) : Thottumkara K. Vinod et al.

It is certified that error appears in the above-identified patent and that said Letters Patent is hereby corrected as shown below:

Column 4,
Line 45, delete the term "generally";

Column 5,
Lines 2 and 16, delete the term "generally".

Signed and Sealed this

Eighteenth Day of October, 2005

JON W. DUDAS
*Director of the United States Patent and Trademark Office*